US009630998B2

(12) United States Patent
Skerra et al.

(10) Patent No.: US 9,630,998 B2
(45) Date of Patent: Apr. 25, 2017

(54) RECOMBINANT BACTERIAL LIPOCALIN BLC AND USES THEREOF

(71) Applicant: Technische Universitaet Muenchen, Munich (DE)

(72) Inventors: Arne Skerra, Freising-Weihenstefan (DE); Andre Schiefner, Nuremberg (DE)

(73) Assignee: Technische Universitaet Muenchen, Munich (DE)

( * ) Notice: Subject to any disclaimer, the term of this patent is extended or adjusted under 35 U.S.C. 154(b) by 16 days.

(21) Appl. No.: 14/620,605

(22) Filed: Feb. 12, 2015

(65) Prior Publication Data

US 2015/0191512 A1    Jul. 9, 2015

Related U.S. Application Data

(62) Division of application No. 13/820,893, filed as application No. PCT/EP2011/065423 on Sep. 7, 2011, now Pat. No. 8,987,415.

(60) Provisional application No. 61/380,521, filed on Sep. 7, 2010.

(51) Int. Cl.
*C07K 14/24* (2006.01)
*C07K 14/245* (2006.01)

(52) U.S. Cl.
CPC .................. *C07K 14/245* (2013.01)

(58) Field of Classification Search
None
See application file for complete search history.

(56) References Cited

U.S. PATENT DOCUMENTS

| 7,250,297 B1 * | 7/2007 | Beste ................... C07K 14/435 435/440 |
| 2005/0106660 A1 * | 5/2005 | Vogt ..................... C07K 14/775 435/69.1 |
| 2006/0058510 A1 | 3/2006 | Skerra et al. |

FOREIGN PATENT DOCUMENTS

| WO | WO-99/16873 A1 | 4/1999 |
| WO | WO-03/029463 A2 | 4/2003 |
| WO | WO-2005/019256 A2 | 3/2005 |

OTHER PUBLICATIONS

Benevenuti et al., "Crystallization of Soluble Proteins in Vapor Diffusion for X-ray Crystallography", Nature Protocols, published on-line Jun. 28, 2007, 2(7):1633-1651.
Beste et al., "Small antibody-like proteins with prescribed ligand specificities derived from the lipocalin fold," Proc. Natl. Acad. Sci. USA, Mar. 1999, 96:1898-1903.
Bishop et al., "The bacterial lipocalins," Biochim Biophys Acta, 2000, 1482:73-83.
Bishop, "Stationary Phase Expression of a Novel *Escherichia coli* Outer Membrane Lipoprotein and Its Relationship with Mammalian Apolipoprotein D," J Biol Chem, Sep. 29, 1995, 270(39):23097-23103.
Breustedt et al., "Comparative ligand-binding analysis of ten human lipocalins," Biochim. Biophys. Acta, 2006, 1764:161-173.
Breustedt et al., "A new crystal form of human tear lipocalin reveals high flexibility in the loop region and induced fit in the ligand cavity," Acta Crystallogr D Biol Crystallogr, 2009, 65:1118-1125.
Bullock et al., "XL1-Blue: A High Efficiency Plasmid Transforming recA *Escherichia coli* Strain with Beta-Galactosidase Selection," Biotechniques, 1987, 5(4):376-378.
Campanacci et al., "The crystal structure of the *Escherichia coli* lipocalin Blc suggests a possible role in phospholipid binding," FEBS Lett, 2004, 562:183-188.
Campanacci et al., "The membrane bound bacterial lipocalin Blc is a functional dimer with binding preference for lysophospholipids," FEBS Lett, 2006, 580:4877-4883.
Collaborative Computational Project, No. 4, "The CCP4 Suite: Programs for Protein Crystallography," Acta Crystallogr, 1994, D50:760-763.
Cudney, "Protein Crystallization and Dumb Luck", The Rigaku Journal, 1999, vol. 16, No. 1, pp. 1-7.
Davis et al., "MolProbity: all-atom contacts and structure validation for proteins and nucleic acids," Nucleic Acids Res, 2007, 35:W375-383.
Drenth, "Principles of Protein X-Ray Crystallography", 2nd Edition, 1999 Springer-Verlag New York Inc., Chapter 1, p. 1-21.
Eichinger et al., "Structural Insight into the Dual Ligand Specificity and Mode of High Density Lipoprotein Association of Apolipoprotein D," J Biol Chem, Oct. 19, 2007, 282(42):31068-31075.
Emsley et al., "Coot: model-building tools for molecular graphics," Acta Crystallogr D Biol Crystallogr, 2004, D60:2126-2132.
Flower et al., "The lipocalin protein family: structural and sequence overview," Biochimica et Biophysica Acta (BBA), Oct. 18, 2000, 1482(1-2):9-24.
Flower, "The lipocalin protein family: structure and function," Biochem. J., 1996, 318:1-14.
Geisselsoder et al., "Efficient Site-Directed In Vitro Mutagenesis," Biotechniques, 1987, 5(8):786-790.
Ghrayeb et al., "Secretion cloning vectors in *Escherichia coli*," EMBO J, 1984, 3(10):2437-2442.
Groat et al., "Starvation proteins in *Escherichia coli*: Kinetics of Synthesis and Role in Starvation Survival," J Bacteriol, 1986, 168:486-493.
Howlin et al., "TLSANL: TLS parameter-analysis program for segmented anisotropic refinement of macromolecular structures," J Appl Crystallogr, 1993: 26:622-624.
Huijbregts et al., "Topology and transport of membrane lipids in bacteria," Biochim Biophys Acta, 2000, 1469:43-61.
Kabsch et al., "Dictionary of Protein Secondary Structure: Pattern Recognition of Hydrogen-Bonded and Geometrical Features," Biopolymers, 1983, 22:2577-2637.

(Continued)

*Primary Examiner* — Suzanne M Noakes
(74) *Attorney, Agent, or Firm* — Foley & Lardner LLP

(57) ABSTRACT

The present inventors have solved the crystal structure of an *Escherichia coli* bacterial lipocalin polypeptide, which depicts a monomeric protein. Previous crystal structures have been reported, but these appear to he inaccurate, as they predicted, e.g., a dimeric protein. The crystal structure of a bacterial lipocalin provided by the present invention leads to numerous uses. For example, the present invention provides for the design, construction and use of recombinant libraries of diversified bacterial lipocalins resulting from a bacterial lipocalin polypeptide "backbone".

3 Claims, 4 Drawing Sheets

(56) References Cited

OTHER PUBLICATIONS

Kabsch, Automatic Processing of Rotation Diffraction Data from Crystals of Initially Unknown Symmetry and Cell Constants, J Appl Crystallogr, 1993, 26:795-800.

Kim et al., "High-Affinity Recognition of Lanthanide(III) Chelate Complexes by a Reprogrammed Human Lipocalin 2," J. Am. Chem. Soc., 2009, 131:3565-3576.

Krissinel et al., "Secondary-structure matching (SSM), a new tool for fast protein structure alighnment in three dimensions," Acta Crystallogr D Biol Crystallogr, 2004, D60:2256-2268.

Krissinel et al., "Inference of Macromolecular Assemblies from Crystalline State," J Mol Biol, 2007, 372:774-797.

Kundrot, "Which Strategy for a Protein Crystallization Project?", Cellular Molecular Life Science, 2004, vol. 61, pp. 525-536.

McPherson, "Current Approaches to Macromolecular Crystallization", European Journal of Biochemistry, 1990, vol. 189, pp. 1-23.

Miller et al., "The accessible surface area and stability of oligomeric proteins," Nature, Aug. 1987, 328(27):834-836.

Moon et al., "A synergistic approach to protein crystallization: Combination of a fixed-arm carrier with surface entropy reduction", Protein Science, 2010, 19:901-913.

Murshudov et al., "Refinement of Macromolecular Structures by the Maximum-Likelihood Method," Acta Crystallogr D Biol Crystallogr, 1997, D53:240-255.

Notice of Allowance dated Nov. 24, 2014 issued in U.S. Appl. No. 13/820,893.

Office Action dated Oct. 22, 2014 issued in U.S. Appl. No. 13/820,893.

Office Action dated Aug. 28, 2014 issued in U.S. Appl. No. 13/820,893.

Schiefner et al., "Structural and biochemical analyses reveal a monomeric state of the bacterial lipocalin Blc," Acta Crystallographica Section D Biological Crystallography, Dec. 1, 2010, 66(12):1308-1315.

Schmidt et al., "The Strep-tag system for one-step purification and high-affinity detection of capturing of proteins," Nat. Protoc., 2007, 2(6):1528-1535.

Schönfeld et al., "An engineered lipocalin specific for CTLA-4 reveals a combining site with structural and conformational features similar to antibodies," Proc. Natl. Acad. Sci. USA, May 19, 2009, 106(20):8198-8203.

Skerra, A., "Phosphorothioate primers improve the amplification of DNA sequences by DNA polymerases with proofreading activity," Nucleic Acids Res, 1992, 20(14):3551-3554.

Skerra, "Lipocalins as a scaffold," Biochim. Et. Biophys. Acta, 2000, vol. 1482, pp. 337-350.

Skerra, "Use of the tetracycline promoter for the tightly regulated production of a murine antibody fragment in *Escherichia coli*," Gene, 1994, 151:131-135.

Storoni et al., "Likelihood-enhanced fast rotation functions," Acta Crystallogr D Biol Crystallogr, 2004, D60:432-438.

Stromer et al., "Analysis of the Regulation of the Molecular Chaperone Hsp26 by Temperature-induced Dissociation," J Biol Chem, Mar. 19, 2004, 279(12):11222-11228.

Tao et al., "Calculating Partition coefficients of Peptides by the Addition Method," J Mol Model, 1999, 5:189-195.

Tokuda et al., "Sorting of lipoproteins to the outer membrane in *E. coli*," Biochim Biophys Acta, 2004, 1693:5-13.

Vogt et al., "Construction of an Artificial Receptor Protein ("Anticalin") Based on the Human Apolipoprotein D," Chembiochem, Feb. 6, 2004, 5(2):191-199.

Winn et al., "Use of TLS parameters to model anisotropic displacements in macromolecular refinement," Acta Crystallogr D Biol Crystallogr, 2001, D57:122-133.

Yanisch-Perron et al., "Improved M13 phage cloning vectors and host strains: nucleotide sequences of the M13mp18 and pUC19 vectors," Gene, 1985, 33:103-119.

Zander et al., "Biochemical characterization of the recombinant human Nogo-A ectodomain," FEBS J, 2007, 274:2603-2613.

\* cited by examiner

Figure 4

ATGAAAAAGACAGCTATCGCGATTGCAGTGGCACTGGCTGGT
MetLysLysThrAlaIleAlaIleAlaValAlaLeuAlaGly

TTCGCTACCGTAGCGCAGGCCGCCAGTTCTCCTACGCCGCCGCGTGGCGTGACCGTAGTA
PheAlaThrValAlaGlnAlaAlaSerSerProThrProProArgGlyValThrValVal

AATAATTTCGACGCCAAACGTTATCTCGGTACCTGGTATGAGATTGCCCGTTTTGATCAC
AsnAsnPheAspAlaLysArgTyrLeuGlyThrTrpTyrGluIleAlaArgPheAspHis

CGCTTTGAACGTGGACTGGAAAAAGTCACCGCAACATACAGCCTGCGTGATGACGGCGGC
ArgPheGluArgGlyLeuGluLysValThrAlaThrTyrSerLeuArgAspAspGlyGly

CTGAATGTCATTAATAAAGGCTATAACCCTGACAGAGGAATGTGGCAGCAGAGTGAAGGG
LeuAsnValIleAsnLysGlyTyrAsnProAspArgGlyMetTrpGlnGlnSerGluGly

AAAGCGTACTTTACCGGCGCACCAACTCGCGCTGCGCTGAAAGTGTCATTCTTTGGTCCT
LysAlaTyrPheThrGlyAlaProThrArgAlaAlaLeuLysValSerPhePheGlyPro

TTCTATGGCGGTTATAACGTTATTGCACTCGATCGGGAATACCGCCATGCGCTGGTTAGC
PheTyrGlyGlyTyrAsnValIleAlaLeuAspArgGluTyrArgHisAlaLeuValSer

GGGCCGGACCGCGACTACCTGTGGATACTCTCCCGCACGCCAACCATTTCTGACGAAGTG
GlyProAspArgAspTyrLeuTrpIleLeuSerArgThrProThrIleSerAspGluVal

AAACAGGAGATGCTGGCAGTCGCGACCCGGGAAGGGTTTGATGTCAGTAAATTTATTTGG
LysGlnGluMetLeuAlaValAlaThrArgGluGlyPheAspValSerLysPheIleTrp

GTACAGCAGCCTGGTAGCGCTTGGTCTCACCCGCAGTTCGAAAAATAA
ValGlnGlnProGlySerAlaTrpSerHisProGlnPheGluLysEnd

SEQUENCE LISTING

```
<160> NUMBER OF SEQ ID NOS: 7

<210> SEQ ID NO 1
<211> LENGTH: 570
<212> TYPE: DNA
<213> ORGANISM: Artificial
<220> FEATURE:
<223> OTHER INFORMATION: Bacterial lipocalin from E. coli with
      N-terminal OmpA signal peptide and C-terminal Strep-tag
<220> FEATURE:
<221> NAME/KEY: CDS
<222> LOCATION: (1)..(567)
<220> FEATURE:
<221> NAME/KEY: sig_peptide
<222> LOCATION: (1)..(63)
<223> OTHER INFORMATION: OmpA signal peptide
<220> FEATURE:
<221> NAME/KEY: misc
<222> LOCATION: (64)..(540)
<223> OTHER INFORMATION: mature bacterial lipocalin
<220> FEATURE:
<221> NAME/KEY: misc
<222> LOCATION: (541)..(567)
```

<223> OTHER INFORMATION: Strep-tag

<400> SEQUENCE: 1

```
atg aaa aag aca gct atc gcg att gca gtg gca ctg gct ggt ttc gct    48
Met Lys Lys Thr Ala Ile Ala Ile Ala Val Ala Leu Ala Gly Phe Ala
1               5                   10                  15 acc gta gcg cag gcc gcc agt tct cct acg ccg ccg cgt ggc gtg acc    96
Thr Val Ala Gln Ala Ala Ser Ser Pro Thr Pro Pro Arg Gly Val Thr
                20                  25                  30 gta gta aat aat ttc gac gcc aaa cgt tat ctc ggt acc tgg tat gag   144
Val Val Asn Asn Phe Asp Ala Lys Arg Tyr Leu Gly Thr Trp Tyr Glu
            35                  40                  45 att gcc cgt ttt gat cac cgc ttt gaa cgt gga ctg gaa aaa gtc acc   192
Ile Ala Arg Phe Asp His Arg Phe Glu Arg Gly Leu Glu Lys Val Thr
        50                  55                  60 gca aca tac agc ctg cgt gat gac ggc ggc ctg aat gtc att aat aaa   240
Ala Thr Tyr Ser Leu Arg Asp Asp Gly Gly Leu Asn Val Ile Asn Lys
65                  70                  75                  80 ggc tat aac cct gac aga gga atg tgg cag cag agt gaa ggg aaa gcg   288
Gly Tyr Asn Pro Asp Arg Gly Met Trp Gln Gln Ser Glu Gly Lys Ala
                85                  90                  95 tac ttt acc ggc gca cca act cgc gct gcg ctg aaa gtg tca ttc ttt   336
Tyr Phe Thr Gly Ala Pro Thr Arg Ala Ala Leu Lys Val Ser Phe Phe
            100                 105                 110 ggt cct ttc tat ggc ggt tat aac gtt att gca ctc gat cgg gaa tac   384
Gly Pro Phe Tyr Gly Gly Tyr Asn Val Ile Ala Leu Asp Arg Glu Tyr
        115                 120                 125 cgc cat gcg ctg gtt agc ggg ccg gac cgc gac tac ctg tgg ata ctc   432
Arg His Ala Leu Val Ser Gly Pro Asp Arg Asp Tyr Leu Trp Ile Leu
    130                 135                 140 tcc cgc acg cca acc att tct gac gaa gtg aaa cag gag atg ctg gca   480
Ser Arg Thr Pro Thr Ile Ser Asp Glu Val Lys Gln Glu Met Leu Ala
145                 150                 155                 160 gtc gcg acc cgg gaa ggg ttt gat gtc agt aaa ttt att tgg gta cag   528
Val Ala Thr Arg Glu Gly Phe Asp Val Ser Lys Phe Ile Trp Val Gln
                165                 170                 175 cag cct ggt agc gct tgg tct cac ccg cag ttc gaa aaa taa           570
Gln Pro Gly Ser Ala Trp Ser His Pro Gln Phe Glu Lys
            180                 185
```

<210> SEQ ID NO 2
<211> LENGTH: 189
<212> TYPE: PRT
<213> ORGANISM: Artificial
<220> FEATURE:
<223> OTHER INFORMATION: Synthetic Construct

<400> SEQUENCE: 2

```
Met Lys Lys Thr Ala Ile Ala Ile Ala Val Ala Leu Ala Gly Phe Ala
1               5                   10                  15

Thr Val Ala Gln Ala Ala Ser Ser Pro Thr Pro Pro Arg Gly Val Thr
                20                  25                  30

Val Val Asn Asn Phe Asp Ala Lys Arg Tyr Leu Gly Thr Trp Tyr Glu
            35                  40                  45

Ile Ala Arg Phe Asp His Arg Phe Glu Arg Gly Leu Glu Lys Val Thr
        50                  55                  60

Ala Thr Tyr Ser Leu Arg Asp Asp Gly Gly Leu Asn Val Ile Asn Lys
65                  70                  75                  80

Gly Tyr Asn Pro Asp Arg Gly Met Trp Gln Gln Ser Glu Gly Lys Ala
                85                  90                  95
```

```
Tyr Phe Thr Gly Ala Pro Thr Arg Ala Ala Leu Lys Val Ser Phe Phe
                100                 105                 110

Gly Pro Phe Tyr Gly Gly Tyr Asn Val Ile Ala Leu Asp Arg Glu Tyr
            115                 120                 125

Arg His Ala Leu Val Ser Gly Pro Asp Arg Asp Tyr Leu Trp Ile Leu
130                 135                 140

Ser Arg Thr Pro Thr Ile Ser Asp Glu Val Lys Gln Glu Met Leu Ala
145                 150                 155                 160

Val Ala Thr Arg Glu Gly Phe Asp Val Ser Lys Phe Ile Trp Val Gln
                165                 170                 175

Gln Pro Gly Ser Ala Trp Ser His Pro Gln Phe Glu Lys
                180                 185

<210> SEQ ID NO 3
<211> LENGTH: 177
<212> TYPE: PRT
<213> ORGANISM: Escherichia coli
<220> FEATURE:
<221> NAME/KEY: misc
<222> LOCATION: (1)..(177)
<223> OTHER INFORMATION: wildtype unprocessed Bacterial lipocalin
<220> FEATURE:
<221> NAME/KEY: SIGNAL
<222> LOCATION: (1)..(18)
<223> OTHER INFORMATION: signal peptide
<220> FEATURE:
<221> NAME/KEY: misc
<222> LOCATION: (19)..(177)
<223> OTHER INFORMATION: mature bacterial lipocalin

<400> SEQUENCE: 3

Met Arg Leu Leu Pro Leu Val Ala Ala Ala Thr Ala Ala Phe Leu Val
1               5                   10                  15

Val Ala Cys Ser Ser Pro Thr Pro Pro Arg Gly Val Thr Val Val Asn
                20                  25                  30

Asn Phe Asp Ala Lys Arg Tyr Leu Gly Thr Trp Tyr Glu Ile Ala Arg
            35                  40                  45

Phe Asp His Arg Phe Glu Arg Gly Leu Glu Lys Val Thr Ala Thr Tyr
50                  55                  60

Ser Leu Arg Asp Asp Gly Gly Leu Asn Val Ile Asn Lys Gly Tyr Asn
65                  70                  75                  80

Pro Asp Arg Gly Met Trp Gln Gln Ser Glu Gly Lys Ala Tyr Phe Thr
                85                  90                  95

Gly Ala Pro Thr Arg Ala Ala Leu Lys Val Ser Phe Phe Gly Pro Phe
                100                 105                 110

Tyr Gly Gly Tyr Asn Val Ile Ala Leu Asp Arg Glu Tyr Arg His Ala
            115                 120                 125

Leu Val Cys Gly Pro Asp Arg Asp Tyr Leu Trp Ile Leu Ser Arg Thr
130                 135                 140

Pro Thr Ile Ser Asp Glu Val Lys Gln Glu Met Leu Ala Val Ala Thr
145                 150                 155                 160

Arg Glu Gly Phe Asp Val Ser Lys Phe Ile Trp Val Gln Gln Pro Gly
                165                 170                 175

Ser

<210> SEQ ID NO 4
<211> LENGTH: 159
<212> TYPE: PRT
<213> ORGANISM: Escherichia coli
```

-continued

```
<220> FEATURE:
<221> NAME/KEY: misc
<222> LOCATION: (1)..(159)
<223> OTHER INFORMATION: mature Bacterial lipocalin (lacking signal
      peptide)

<400> SEQUENCE: 4
```

Cys Ser Ser Pro Thr Pro Pro Arg Gly Val Thr Val Val Asn Asn Phe
1               5                   10                  15

Asp Ala Lys Arg Tyr Leu Gly Thr Trp Tyr Glu Ile Ala Arg Phe Asp
            20                  25                  30

His Arg Phe Glu Arg Gly Leu Glu Lys Val Thr Ala Thr Tyr Ser Leu
        35                  40                  45

Arg Asp Asp Gly Gly Leu Asn Val Ile Asn Lys Gly Tyr Asn Pro Asp
    50                  55                  60

Arg Gly Met Trp Gln Gln Ser Glu Gly Lys Ala Tyr Phe Thr Gly Ala
65                  70                  75                  80

Pro Thr Arg Ala Ala Leu Lys Val Ser Phe Phe Gly Pro Phe Tyr Gly
                85                  90                  95

Gly Tyr Asn Val Ile Ala Leu Asp Arg Glu Tyr Arg His Ala Leu Val
            100                 105                 110

Cys Gly Pro Asp Arg Asp Tyr Leu Trp Ile Leu Ser Arg Thr Pro Thr
        115                 120                 125

Ile Ser Asp Glu Val Lys Gln Glu Met Leu Ala Val Ala Thr Arg Glu
    130                 135                 140

Gly Phe Asp Val Ser Lys Phe Ile Trp Val Gln Gln Pro Gly Ser
145                 150                 155

```
<210> SEQ ID NO 5
<211> LENGTH: 20
<212> TYPE: DNA
<213> ORGANISM: artificial
<220> FEATURE:
<223> OTHER INFORMATION: oligonucleotide used for the amplification of
      Blc

<400> SEQUENCE: 5
ccagttctcc tacgccgccg                                              20

<210> SEQ ID NO 6
<211> LENGTH: 20
<212> TYPE: DNA
<213> ORGANISM: artificial
<220> FEATURE:
<223> OTHER INFORMATION: oligonucleotide used for the amplification of
      Blc

<400> SEQUENCE: 6
gctaccaggc tgctgtaccc                                              20

<210> SEQ ID NO 7
<211> LENGTH: 25
<212> TYPE: DNA
<213> ORGANISM: artificial
<220> FEATURE:
<223> OTHER INFORMATION: oligonucleotide used for the introduction of a
      Cys to Ser replacement in Blc

<400> SEQUENCE: 7
ggtccggccc gctaaccagc gcatg                                        25
```

RECOMBINANT BACTERIAL LIPOCALIN BLC AND USES THEREOF

CROSS-REFERENCE TO RELATED APPLICATIONS

This application is a Divisional of U.S. Ser. No. 13/820,893, filed Aug. 22, 2013 (now pending), which is a National Stage application of PCT/EP2011/065423, filed Sep. 7, 2011, which claims the benefit of U.S. Provisional Application No. 61/380,521, filed Sep. 7, 2010.

The instant application contains a Sequence Listing which has been submitted in ASCII format via EFS-WEB and is hereby incorporated by reference in its entirety. Said ASCII copy, created on Mar. 4, 2013, is named sequence.txt and is 10 KB.

BACKGROUND

Lipocalins represent a family of functionally diverse, small proteins comprising 160-180 residues that share high conservation at the tertiary structural level while having weak amino acid sequence homology (Flower et al., 2000; Skerra, 2000). Their fold is dominated by an eight-stranded antiparallel β-barrel with an α-helix attached to its side, whereby four structurally variable loops, which connect neighboring β-strands at the open end of the barrel, form the entrance to a ligand pocket. Further hallmarks are three structurally conserved regions (SCRs) (Flower, 1996), which assist the identification of new lipocalins at the primary structure level.

Lipocalins were initially described for eukaryotes and only more recently identified in Gram-negative bacteria (Flower, 1996; Bishop, 2000). The bacterial lipocalin (Blc) was first discovered in *Escherichia coli* (Bishop et al., 1995), but sequence analyses have indicated the existence of at least 20 other bacterial lipocalins, for example in *Citrobacter freundii*, *Vibrio cholerae* and many other Enterobacteriaceae.

Blc belongs to the class I outer membrane lipoproteins, carrying a type II signal peptide at the N-terminus, which directs export into the periplasm. After signal peptide processing, the protein becomes anchored into the inner leaflet of the outer membrane (Bishop et al., 1995) via a lipid-modified amino-terminal cysteine residue. The blc promoter is mainly induced at the onset of the stationary growth phase via the rpoS sigma factor, which generally directs gene expression for adaptation to starvation and high osmolarity or other conditions known to exert stress on the cell envelope. The blc gene is poorly transcribed, suggesting that the normal concentration of Blc in the outer membrane is low.

Other findings indicate an implication of Blc in bacterial host pathogenesis (Bishop, 2000). The blc genes of some Enterobacteriaceae are physically linked to the ampC gene, which encodes a serine β-lactamase on the chromosome but also appears to be genetically recombined into different plasmids. This co-localisation suggests that the blc gene may be involved in antibiotic resistance. Furthermore, bacterial lipocalins play a role in the host immune response as many components of the bacterial cell envelope provide so-called pathogen-associated molecular patterns for surveillance. One relevant component is the N-acyl-S-sn-1,2-diacylglycerylcysteine modification at the N-terminus of the bacterial lipoproteins, permitting macrophages and other immune cells to recognize Blc via CD14 and the Toll-like receptor 2.

The first crystal structure of an N-terminally extended version of a Blc, so-called Blc-X (Campanacci et al. 2004), revealed the β-barrel fold characteristic for the lipocalin family and was followed by a second crystal structure of Blc-X in complex with the fatty acid vaccenic acid (Campanacci et al., 2006). Both structures belong to the space group $P2_12_12_1$ with isomorphous unit cell parameters and an overall r.m.s. deviation of 0.1 Å for 167 Cα atoms.

The crystal structures of Campanacci et al. indicated that Blc was a dimeric protein. This prediction was based on the identification of a tight pairwise contact of several side chains and a buried surface of 786 Å$^2$ and 825 Å$^2$, respectively, of the two distinct Blc-X molecules A and B within the asymmetric unit, and also on static light scattering measurements in solution. Notably, the fatty acid ligand was bound in the cavity of just one molecule of the dimer and involved in only a few additional contacts to the other molecule, which was explained by the asymmetric interaction of the two Blc-X monomers. Yet, binding of vaccenic acid did not lead to detectable conformational changes within the Blc-X dimer (Campanacci et al., 2006).

The present inventors, however, studied the biochemistry and structure of a recombinant Blc without N-terminal extension overproduced with a different *E. coli* expression vector, and found striking evidence that Blc behaves as a stable monomer in solution. The previously described dimerization is, therefore, likely the result of a cloning artifact. This surprising finding is one of the bases of the present invention.

SUMMARY OF THE INVENTION

The present invention can be summarized by the following items

1. A method of preparing a plurality of nucleic acid molecules, comprising the step of (i) synthesizing or (ii) recombinantly producing a plurality of nucleic acid molecules, wherein said molecules differ from each other in at least one nucleotide at a position within at least one loop region of the nucleic acid encoding a Blc polypeptide.
2. A method according to item I, comprising the step of synthesizing or recombinantly producing at least six different nucleic acid molecules,
3. A method according to any one of the preceding items, wherein said molecules differ from each other in at least one nucleotide at a position within at least two loop regions of the nucleic acid encoding said Blc polypeptide.
4. A method according to any one of the preceding items, wherein said molecules differ from each other in at least one nucleotide at a position within at least three loop regions of the nucleic acid encoding said Blc polypeptide.
5. A method according to any one of the preceding items, wherein said molecules differ from each other in at least one nucleotide at a position within at least four loop regions of the nucleic acid encoding said Blc polypeptide.
6. A method according to any one of the preceding items, wherein said molecules differ from each other in at least one nucleotide at a position within the nucleotides encoding amino acid residue positions 88-96 of said Blc polypeptide, and wherein said molecules encode different polypeptides from each other.
7. A method according to any one of the preceding items, wherein said molecules differ from each other in at least one nucleotide at a position within the nucleotides encoding amino acid residue positions 27-43 of said Blc polypeptide, and wherein said molecules encode different polypeptides from each other.

8. A method according to any one of the preceding items, wherein said molecules differ from each other in at least one nucleotide at a position within the nucleotides encoding amino acid residue positions 58-73 of said Blc polypeptide, and wherein said molecules encode different polypeptides from each other.

9. A method according to any one of any one of the preceding items, wherein said molecules differ from each other in at least one nucleotide at a position within the nucleotides encoding amino acid residue positions 113-121 of said Blc polypeptide and wherein said molecules encode different polypeptides from each other.

10. A method of preparing a plurality of polypeptide molecules, comprising the steps of expressing the plurality of nucleic acid molecules according to any one of the preceding items.

11. A composition comprising a plurality of nucleic acid molecules, wherein said molecules differ from each other in at least one nucleic acid nucleotide at a position within at least one loop region of the nucleic acid encoding a Blc polypeptide.

12. A composition according to item 11, wherein said plurality comprises at least six different nucleic acid molecules.

13. A composition according to item 11 or 12, wherein said nucleic acid molecules differ from each other in at least one nucleotide at a position within at least two loop regions of the nucleic acid encoding said Blc polypeptide.

14. A composition according to any one of items 11 to 13, wherein said molecules differ from each other in at least one position within at least three loop regions of the nucleic acid encoding said Blc polypeptide.

15. A composition according to any one of items 11 to 14, wherein said molecules differ from each other in at least one nucleotide at a position within at least four loop regions of the nucleic acid encoding said Blc polypeptide.

16. A composition according to any one of items 11 to 15, wherein said molecules differ from each other in at least one nucleotide at a position within the nucleotides encoding amino acid residue positions 88-96 of said Blc polypeptide, and wherein said molecules encode different polypeptides from each other.

17. A composition according to any one of items 11 to 16, wherein said molecules differ from each other in at least one nucleotide at a position within the nucleotides encoding amino acid residue positions 27-43 of said Blc polypeptide.

18. A method according to any one of items 11 to 17, wherein said molecules differ from each other in at least one nucleotide at a position within the nucleotides encoding amino acid residue positions 58-73 of said Blc polypeptide 19. A method according to any one of items 11 to 18, wherein said molecules differ from each other in at least one nucleotide at a position within the nucleotides encoding amino acid residue positions 113-121 of said Blc polypeptide.

20. A composition comprising a plurality of polypeptide molecules, wherein said polypeptide molecules differ from each other in at least one amino acid at a position within at least one loop region of a Blc polypeptide.

21. A composition according to item 20, wherein said plurality comprises at least six different polypeptide molecules.

22. A composition according to item 20 or 21, wherein said polypeptide molecules differ from each other in at least one amino acid at a position within at least two loop regions of said Blc polypeptide.

23. A composition according to any one of items 20 to 22, wherein said polypeptide molecules differ from each other in at least one amino acid at a position within at least three loop regions of said Blc polypeptide.

24. A composition according to any one of items 20 to 23, wherein said polypeptide molecules differ from each other in at least one amino acid at a position within at least four loop regions of said Blc polypeptide 25. A composition according to any one of items 20 to 24, wherein said molecules differ from each other in at least one amino acid position within amino acid residue positions 88-96 of said Blc polypeptide.

26. A composition according to any one of items 20 to 25, wherein said molecules differ from each other in at least one amino acid position within amino acid residue positions 27-43 of said Blc polypeptide.

27. A method according to any one of items 20 to 26, wherein said molecules differ from each other in at least one amino acid position within amino acid residue positions 58-73 of said Blc polypeptide 28. A method according to any one of items 20 to 27, wherein said molecules differ from each other in at least one amino acid position within amino acid residue positions 113-121 of said Blc polypeptide.

29. A method of isolating a polypeptide of interest, comprising the steps of (i) allowing the composition of any one of items 20 to 28 to be in contact with a target of interest, wherein said polypeptide of interest is comprised within said composition and specifically binds to the target; and (ii) isolating the polypeptide or a polypeptide-target complex resulting from said specific binding 30. A method of isolating a nucleic acid molecule of interest, comprising the steps of (i) allowing the composition of any one of items 20 to 28 to be in contact with a target of interest, where said polypeptide is comprised within said composition and specifically binds to the target; (ii) isolating the polypeptide or a polypeptide-target complex resulting from said specific binding; (iii) isolating the nucleic acid sequence encoding said polypeptide; and (iv) determining the nucleic acid encoding said polypeptide.

31. A crystal structure of a monomeric Blc polypeptide.

32. A crystal structure according to item 31, wherein said structure is depicted in FIG. 3.

33. A method according to any one of items 1-10, 18-17, and 27-30 wherein said molecules are selected from a group consisting of at least 50%, at least 60%, at least 75%, at least 90%, at least 95%, or at least 99 sequence identity with SEQ-ID NO. 1, 34. A composition according to any one of items 11-17 and 20-26 wherein said molecules are selected from a group consisting of at least 50%, at least 60%, at least 75%, at least 90%, at least 95%, or at least 99% sequence identity with SEQ-ID NO. 1.

35. An isolated crystalline form of a monomeric Blc polypeptide

36. An isolated crystalline form of item 35, wherein said crystalline form has a I4122 space group and unit cell dimensions a=b=88.9, c=78.4.

BRIEF DESCRIPTION OF THE DRAWINGS

FIG. 4: SEQ ID NO. 1: Full length recombinant Blc as encoded on pBlc2, including the OmpA signal peptide (amino acid residues 1-21) and the C-terminal Strep-tag. SEQ ID NO. 2: Amino acid sequence of full length recombinant Blc as encoded by SEQ ID NO. 1.

DETAILED DESCRIPTION

Unless otherwise specified, "a" or "an" means "one or more." The disclosure illustratively described herein may suitably be practiced in the absence of any element or elements, limitation or limitations, not specifically disclosed herein. Thus, for example, the terms "comprising", "including," containing", etc. shall be read expansively and without limitation. Also, the term "comprising" when used herein can be replaced by the term "consisting of". Additionally, the terms and expressions employed herein have been used as terms of description and not of limitation, and there is no intention in the use of such terms and expressions of excluding any equivalents of the features shown and described or portions thereof, but it is recognized that various modifications are possible. Thus, it should be understood that although the present disclosure has been specifically disclosed by exemplary embodiments and optional features, modification and variation of the disclosures embodied therein herein disclosed may be resorted to by those skilled in the art, and that such modifications and variations are considered to be within the scope of this disclosure. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

Figure 1:
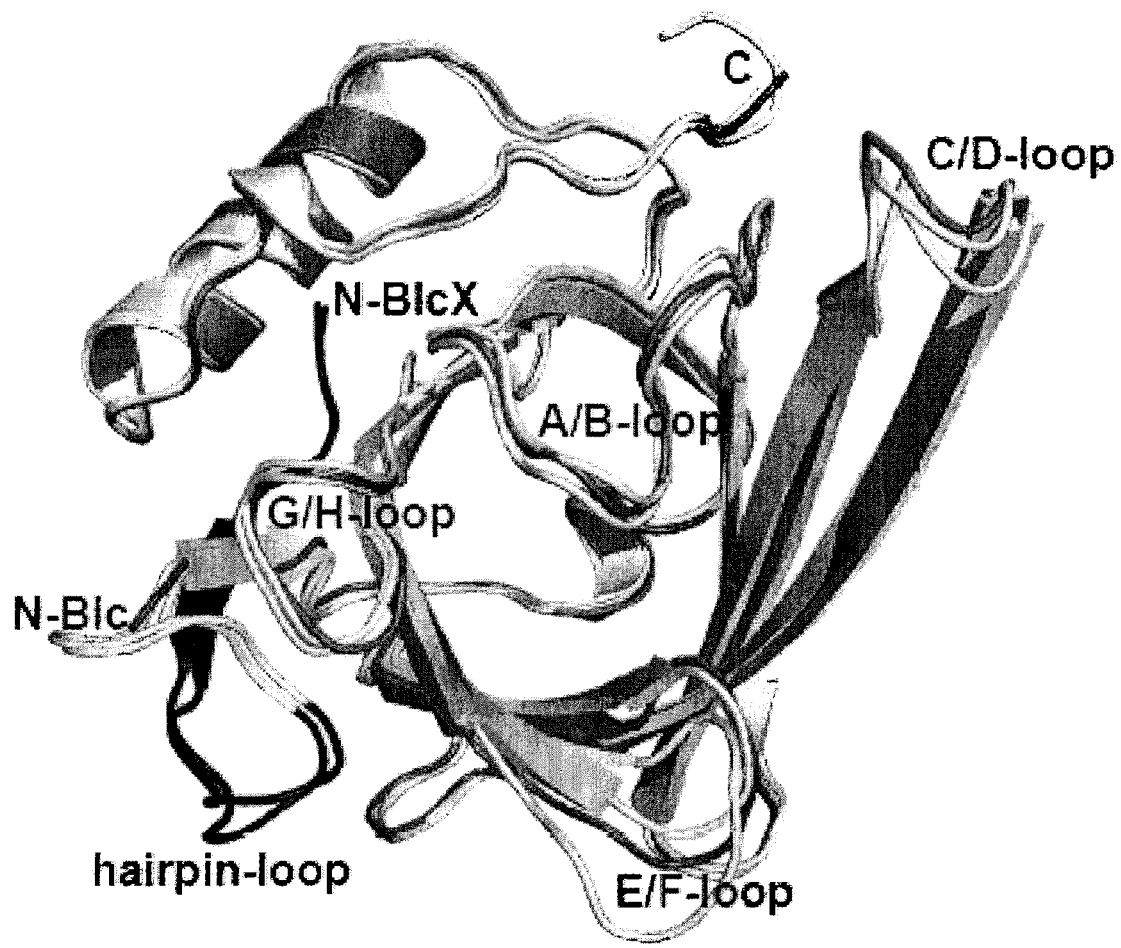
FIG. 1: Comparison of Blc (dark grey) crystallized in space group $I4_122$, with Blc-X (light grey) crystallized in space group $P2_12_12_1$ (PDB entry 2ACO, depicting the two monomers in the asymmetric unit) after superposition of the 149 Cα positions resolved for all structures. The previously published structure of Blc-X reveals a long N-terminal extension including an additional β-strand and a hairpin loop (black). N-Blc denotes the first residue visible in the crystal structure for Blc, N-BlcX denotes the first residue visible in the crystal structure for Blc-X, C labels the C-termini of all three structures shown.

The present inventors have solved the crystal structure of a particular *Escherichia coli* bacterial lipocalin (Blc), as depicted in dark grey in FIG. 1, which allows for several novel application as further described herein. As used herein, "Blc" is defined as any bacterial lipocalin, including but not limited to the bacterial lipocalin having SwissProt Entry P0A901. Blc polypeptides comprise a class of polypeptides that belongs to the class I outer is membrane lipoproteins, carrying a type II signal peptide at the N-terminus which allows export into the periplasm. The amino acid sequence of the Blc polypeptide is shown in SEQ ID NO.3, with amino acids 1-18 representing the type II signal peptide and amino acids 19-177 representing the mature bacterial lipocalin protein. After signal peptide processing, the protein becomes anchored into the inner leaflet of the outer membrane (Bishop et al., 1995) via a lipid-modified amino-terminal cysteine residue. SEQ ID NO. 4 shows the amino acid sequence of the mature bacterial lipocalin protein.

Accordingly, the invention relates to a method of preparing a plurality of nucleic acid molecules, comprising the step of (i) synthesizing or (ii) recombinantly producing a plurality of nucleic acid molecules, wherein said molecules differ from each other in at least one nucleotide at a position within at least one loop region of the nucleic acid encoding a Blc polypeptide. The nucleic acids of the plurality of nucleic acids encode one or more bacterial lipocalin (Blc) muteins.

Also, the invention relates to a composition comprising a plurality of nucleic acid molecules, wherein said molecules differ from each other in at least one nucleic acid nucleotide at a position within at least one loop region of the nucleic acid encoding a Blc polypeptide. Similarly, the invention relates to a plurality of polypeptide molecules, wherein said polypeptide molecules differ from each other in at least one amino acid at a position within at least one loop region of a Blc polypeptide. These polypeptide molecules are in the sense of the invention bacterial lipocalin muteins.

Additional embodiments relate to novel crystals of monomer Blc.

The amino acid sequence shown in SEQ ID NO 1 (or 2) comprises at amino acid position 22-180 the mature bacterial lipocalin protein, while amino acids 1-21 represent the type I OmpA signal peptide and amino acids 181-189 represent the Strep-tag II For the purpose of the present invention whenever reference is made to bacterial lipocalin, the mature bacterial lipocalin shown, for example, in SEQ ID NO. 1 at amino acid positions 22-180), SEQ ID NO. 2 at amino acid positions 22-180, SEQ ID NO. 3 at amino acid positions 19-177 or SEQ ID NO. 4 at amino acid positions 1-159 is meant. Thus, when locating, for example, the amino acid residue positions 27-43, 58-73, 88-96 or 113-121 of the loops of the bacterial lipocalin of the present invention should be located, the starting point for counting is in SEQ ID NO. 1 and SEQ ID NO. 2 amino acid position 22 (i.e., position 22 of SEQ ID NO. 1 or 2 is position "I" for that purpose), in SEQ ID NO. 3 amino acid position 19 (i.e., position 19 of SEQ ID NO. 3 is position "1" for that purpose) and in SEQ ID NO. 4 amino acid position 1 (i e., position 1 of SEQ ID NO. 4 is position "1" for that purpose).

In one aspect, the present invention relates to a library of functional polypeptides that is based on the Blc lipocalin; accordingly, the invention includes polypeptides that have at least 50%, preferably at least 75%, more preferably at least 90%, and most preferably at least 99 sequence identity with SEQ. ID NO. 1 or 3. It is preferred that the degree of identity is determined over the full length of the sequence being compared. It is also preferred that polypeptides that have the degree identity as described herein with SEQ ID NO. 1 or 3 have one or more amino acid replacements, in particular in the loops (1, 2, 3 and/or 4) in comparison to the wildtype bacterial lipocalin. The use of various lipocalins as a "progenitor" to develop a library of lipocalin polypeptides that have diversified amino acids compared to the progenitor has been described (see, e.g., Beste et al, (1999)). Indeed, libraries of human lipocalin-derived proteins, called Anticalins, have led to the isolation of several therapeutically relevant drug candidates (see, e.g. WO05/019256, WO06/056464).

Prior to the proper elucidation of the Blc polypeptide by the present inventors, however, a rational design of a diverse library of Blc-derived Anticalins was not possible. For instance, based on the previously proposed crystal structure of Blc, Campanacci et al predicted that Blc would former homodimers, which would not have motivated the skilled worker to design a library based on Blc, given, e.g., the inherent complexities of utilizing a dimeric lipocalin over the known monomeric lipocalins whose structures already have been solved.

Figure 2:
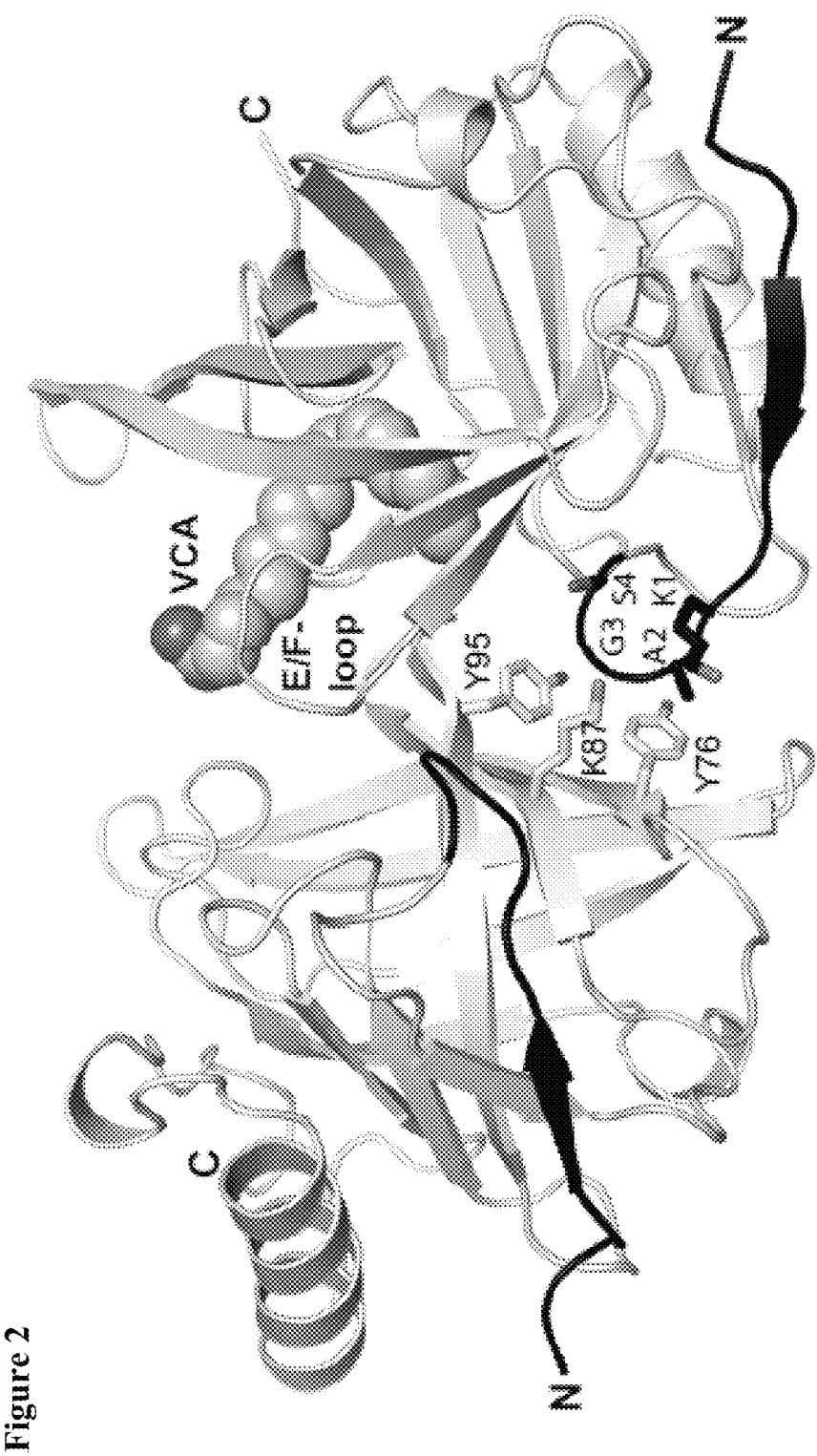
FIG. 2: Analysis of the dimer interface in the previously described Blc-X crystal structure with two monomers in the asymmetric unit (PDB entry 2ACO). The ligand vaccenic acid (labeled VCA, grey spheres) occupies only one ligand pocket. The N-terminal peptide extension of Blc-X, which includes the hairpin loop and the additional β-strand outside the β-barrel, is colored black for both monomers. The four mutated residues within the hairpin loop of Blc-X (Lys-Ala-Gly-Ser), whose sequence positions correspond to the four N-terminal amino acids of mature wild-type Blc, are depicted with side chains and labeled for the rightmost monomer B. This segment of molecule B forms direct contacts with three side chains (Tyr94, Lys105, Tyr113) displayed on the β-barrel surface of molecule A (left). Next to this interaction, the E/F-loops of both molecules form another tight, almost symmetrical contact. N- and C-termini of the polypeptide chains are labeled.

According to the previously reported structures, as shown in FIG. 2, the skilled worker would have been motivated, for example, against diversifying the E/F and G/H loop regions in a library of diversified Blc polypeptides, as the skilled worker would have expected these regions to form part of or be close to, the interface of the proposed Blc dimer.

Accordingly, an accurate crystal structure of a bacterial lipocalin, which is one aspect of the present invention, provides numerous applications, which also are provided by the present invention. For example, the present invention provides for the design, construction and use of recombinant libraries of diversified bacterial lipocalins (including nucleic acid molecules encoding the same) modelled after a bacterial lipocalin polypeptide "backbone" such as Blc. Techniques for recombinantly producing proteins are known to those skilled in the art (e.g. Skerra, A. (2001)).

Thus, in general, the present invention contemplates a monomeric Blc protein having the amino acid sequence shown in SEQ ID NO. 3. Also, it is generally preferred that the bacterial lipocalin muteins of the present invention are monomeric.

In one embodiment, the present invention provides a method of preparing a plurality of nucleic acid molecules that are based on a Blc polypeptide and that differ from each other. As used herein, a "plurality" is defined as two or more. In a preferred embodiment, the plurality includes at least six nucleic molecules and may include at least 50, 10^2, 10^3, 10^4, 10^5, 10^6, 10^7, 10^8, 10^9, 10^10, or at least 10^11 nucleic acid molecules.

The present invention also contemplates a method of preparing a plurality of polypeptide molecules that are based on a Blc polypeptide and that differ from each other. In this sense, the present invention includes a method of expressing the plurality of nucleic acids molecules that are based on a Blc polypeptide and contemplated herein.

Additionally, the present invention provides compositions that include a plurality of nucleic acid molecules that are based on a Blc polypeptide and that differ from each other. Within the plurality of nucleic acid molecules contemplated by the present invention (as well as the methods described herein), the molecules may differ from each other in any region. The plurality of nucleic acid molecules may, for example, differ in a loop region of a Blc polypeptide. In this sense, the plurality of nucleic acid molecules may, for instance, differ in at least one nucleotide at a position within one, two, three and/or four loop regions of the nucleic acid encoding a Blc polypeptide. These positions may, but are not required to, include at least one nucleotide at a position within the nucleotides encoding amino acid residue positions 27-43, 58-73, 88-96, 113-121 of a Blc polypeptide. Preferably, said molecules, substantially all of said molecules or the majority of said molecules encodes different polypeptides from each other. As used herein, a "loop region" of a Blc polypeptide is defined as a peptide segment which joins two adjacent β-strands that form part of the β-barrel in the lipocalin structure, which may include adjoining parts of the β-strands themselves. Examples for such loop regions are the segments comprising amino acid residue positions 27-43, 58-73, 88-96 or 113-121 of a Blc polypeptide.

The amino acid sequence for wild type Blc, including its signal sequence, (SEQ ID NO:3) is:

```
  1 mrllplvaaa taaflvvaCS SPTPPRGVTV VNNFDAKRYL GTWYEIARFD HRFERGLEKV
 61 TATYSLRDDG GLNVINKGYN PDRGMWQQSE GKAYFTGAPT RAALKVSFFG PFYGGYNVIA
121 LDREYRHALV CGPDRDYLWI LSRTPTISDE VKQEMLAVAT REGFDVSKFI WVQQPGS
```

The lower-case letters represent the signal peptide, while the underlined letters represent the Blc loops that can be randomized according to the present invention.

Additionally, the present invention provides compositions that include a plurality of polypeptides. In this sense, the present invention provides, for example, compositions that include a plurality of amino acid sequences that are based on a Blc polypeptide and that differ from each other. Within the plurality of polypeptides and, hence, amino acid sequences contemplated by the present invention (as well as the methods described herein), the molecules may differ from each other in any region. The plurality of polypeptides may, for example, differ in a loop region of a Blc polypeptide. In this sense, the plurality of polypeptides may, for instance, differ in at least one amino acid at a position within one, two, three and/or four loop regions of a Blc polypeptide. These positions may, but are not required to, include at least one position within the amino acid residue positions 27-43, 58-73, 88-96, 113-121 of a Blc polypeptide. Preferably, said molecules, substantially all of said molecules or the majority of said molecules encodes different polypeptides from each other.

Figure 3:
FIG. 3: Crystalline structure of the invention elucidated by X-ray diffraction. Amino acid positions 27-43, 58-73, 88-96, 113-121 represent the loop regions of the mature *E. coli* Blc.

The present invention also contemplates the preparation of a library of Blc variants that contains a plurality of polypeptide molecules, where polypeptide molecules may contain one or more different amino acids (vis-a-vis a mature Blc polypeptide) within any or all of the 4 loop region positions, as delineated in FIG. 3.

The present invention also provides a method of isolating a polypeptide of interest, as described in Kim et al. (2009) and Schönfeld et al. (2009). In one aspect, this includes a step of allowing a composition of the present invention to be in contact with a target of interest. To this end, a polypeptide of interest is comprised within the composition and specifically binds to the target. As used herein, a "target" is defined as any molecule to which a polypeptide of the invention is capable of specifically binding, including all types of proteinaceous and non-proteinacious molecules such as haptens or other small molecules. As used herein, a polypeptide of the invention "specifically binds" a target if it is able to discriminate between that target and one or more reference targets, since binding specificity is not an absolute, but a relative property, "Specific binding" can be determined, for example, in accordance with Western blots, ELISA-, RIA-, ECL-, IRMA-tests, FACS, IHC and peptide scans. The polypeptide of the invention can bind to the target with an affinity in the micromolar or, in more preferred embodiments, in the nanomolar range. Binding constants of less than 100 µM, 50 µM, 500 nM, 250 nM, 100 nM and 50 nM are also envisioned for the current invention.

According to this method, a polypeptide that specifically binds to a target of interest is preferably isolated, which can be accomplished according to conventional techniques, such as those defined in Kim et al. (2009) and Schönfeld et al. (2009), which typically involve the selection of a polypeptide of interest (phenotype) that is linked to its underlying genetic code (genotype). For instance, the polypeptide of interest may be expressed and then selected as part of any conventional selection technology, for example, a technology that involves a replicable genetic package, such as a bacteriophage. These technologies include, for example, display technologies such as phage display and cell surface display. In vitro selection technologies, such as ribosome display, also may be used. See, e.g., Kawasaki, U.S. Pat. Nos. 5,643,768 and 5,658,754.

The present invention also provides a crystal structure of a monomeric Blc polypeptide. In a particular embodiment, the present invention includes the crystal structure is depicted in FIGS. 1 and 3. The present invention also includes a Blc crystal being characterized by the data shown in Table 1.

A preferred embodiment of the method for preparing a plurality of nucleic acid molecules includes the generation of a mutein of a bacterial lipocalin protein, said mutein having detectable affinity to a given target, comprising the step of (a) subjecting the bacterial lipocalin to mutagenesis at one or more of the sequence positions which correspond to the sequence positions 27 to 43 (loop 1), 58-73 (loop 2), 88-96 (loop 3) and/or 113 to 121 (loop 4) of SEQ ID NO. 3, resulting in one or more mutein (s) of the bacterial lipocalin protein.

In a preferred embodiment, said method further comprises step (b) enriching at least one resulting mutein having binding affinity for a given target from the one or more muteins by selection and/or isolating said at least one mutein.

Preferably, the mutagenesis in step (a) of the method for generating a mutein of a bacterial lipocalin results in a plurality of muteins of the protein.

It is also a preferred embodiment of the present invention that further amino acids of the bacterial lipocalin protein (apart from those comprised by the four loops) are subjected to mutagenesis in the above method.

The composition of the present invention comprising a plurality of polypeptide molecules preferably includes a Blc mutein in which one or more amino acids within one, two, three, or all four loops are changed in comparison to the wildtype (or reference) Blc of the present invention. Said one or more amino acids include 1, 2, 3, 4, 5, 6, 7, 8, 9, 10, 11, 12, 13, 14, 15, 16, 17, 18, 19, 20 or more amino acids that can be changed in loop 1, loop 2, loop 3 and loop 4 However, it is also envisaged that within loop 1 1, 2, 3, 4, 5, 6, 7, 8, 9, 10, 11, 12, 13, 14, 15, 16, or 17; within loop 2 1, 2, 3, 4, 5, 6, 7, 8, 9, 10, 11, 12, 13, 14, 15, or 16; within loop 3 1, 2, 3, 4, 5, 6, 7, 8, or 9; and/or within loop 4 1, 2, 3, 4, 5, 6, 7, 8, or 9 amino acids are replaced. "Replacement" means that an amino acid different from that present at the corresponding position in the wildtype (or reference) bacterial lipocalin is present in a bacterial lipocalin of the present invention, The present invention also envisages a bacterial lipocalin other than Blc in which one or more amino acids within one, two, three, or all four loops are changed in comparison to the wildtype (or reference) bacterial lipocalin of the present invention. Said one or more amino acids include 1, 2, 3, 4, 5, 6, 7, 8, 9, 10, 11, 12, 13, 14, 15, 16, 17, 18, 19, 20 or more amino acids that can be changed in loop 1, loop 2, loop 3 and loop 4. However, it is also envisaged that within loop 1 1, 2, 3, 4, 5, 6, 7, 8, 9, 10, 11, 12, 13, 14, 15, 16, or 17; within loop 2 1, 2, 3, 4, 5, 6, 7, 8, 9, 10, 11, 12, 13, 14, 15, or 16; within loop 3 1, 2, 3, 4, 5, 6, 7, 8, or 9; and/or within loop 4 1, 2, 3, 4, 5, 6, 7, 8, or 9 amino acids are replaced.

The loops of a bacterial lipocalin other than Blc can be readily identified by the skilled person as described herein. Briefly, the skilled person can align the Blc of the present invention and an amino acid sequence of interest that is assumed to be a bacterial lipocalin so as to determine (i) the degree of identity and/or (ii) the position of the loops that correspond to those of the loops of Blc.

When used herein, a "mutein," a "mutated" entity (whether protein or nucleic acid) or "mutant" refers to the exchange, deletion, or insertion of one or more nucleotides or amino acids, respectively, within the bacterial lipocalin protein (Blc) of the present invention compared to the naturally occurring (wild-type) nucleic acid or protein "reference" scaffold of Blc, for example, shown in SEQ ID NO. 3.

Accordingly, a mutein of the invention may include the wild type (natural) amino acid sequence of the "parental" protein scaffold (bacterial lipocalin (Blc)) outside the mutated one or more amino acid sequence positions within one, two, three or four loop(s); alternatively, a bacterial lipocalin mutein may also contain amino acid mutations outside the sequence positions subjected to mutagenesis that do not interfere with the binding activity and the folding of the mutein. Such mutations can be accomplished on a DNA level using established standard methods (Sambrook, J. et al. (2001) *Molecular Cloning: A Laboratory Manual*, 3$^{rd}$ Ed., Cold Spring Harbor Laboratory Press, Cold Spring Harbor, N.Y.). Possible alterations of the amino acid sequence are insertions or deletions as well as amino acid substitutions.

Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of a parental protein scaffold, where these deletions or insertion result in a stable folded/functional mutein, which can be readily tested by the skilled worker.

The skilled worker will appreciate methods useful to prepare protein muteins contemplated by the present invention but whose protein or nucleic acid sequences are not explicitly disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein for a given target. Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

Accordingly, the invention also includes functional variants of muteins disclosed herein, which have a threshold sequence identity or sequence homology to a reference protein. By "identity" or "sequence identity" is meant a property of sequences that measures their similarity or relationship. The term "sequence identity" or "identity" as used in the present invention means the percentage of pair-wise identical residues—following (homologous) alignment of a sequence of a polypeptide of the invention with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of two proteins. Most preferred, the amino acid sequence shown in SEQ ID NO. 3 is preferred as a "reference sequence". SEQ ID NO. 3 shows the mature bacterial lipocalin protein (Blc). The term "reference sequence" and "wild type sequence" (of Blc) is used interchangeably herein.

As mentioned herein, the present invention relates to polypeptides that share a certain degree of identity with the bacterial lipocalin protein (Blc) of the present invention. Such polypeptides comprise preferably one or more amino acid replacements in comparison to the wildtype Blc amino acid sequence.

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-1}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

It is also possible to deliberately mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages. With respect to a mutein of human Lipocalin 2, exemplary possibilities of such a mutation to introduce a cysteine residue into the amino acid sequence of a bacterial lipocalin mutein.

The term "position" when used in accordance with the invention means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the invention which may be substituted may vary due to deletion or addition of amino acids elsewhere in a (mutant or wild-type) lipocalin. Similarly, the position of a given nucleotide in accordance with the present invention which may be substituted may vary due to deletions or additional nucleotides elsewhere in a mutein or wild type bacterial lipocalin 5'-untranslated region (UTR) including the promoter and/or any other regulatory sequences or gene (including exons and introns).

Thus, under a "corresponding position" in accordance with the invention it is preferably to be understood that nucleotides/amino acids may differ in the indicated number but may still have similar neighboring nucleotides/amino acids. Said nucleotides/amino acids which may be exchanged, deleted or added are also comprised by the term "corresponding position". When used herein "at a position corresponding to a position" a position in a "query" amino acid (or nucleotide) sequence is meant that corresponds to a position in a "subject" amino acid (or nucleotide) sequence.

Specifically, in order to determine whether a nucleotide residue or amino acid residue of the amino acid sequence of a bacterial lipocalin different from a bacterial lipocalin mutein of the invention corresponds to a certain position in the nucleotide sequence or the amino acid sequence of a bacterial lipocalin mutein as described, in particular any of SEQ ID NOs. 1-4, a skilled artisan can use means and methods well-known in the art, e.g., alignments, either manually or by using computer programs such as BLAST 2.0 (Altschul et al. (1990), J. Mol. Biol. 215:403-10), which stands for Basic Local Alignment Search Tool, or ClustalW (Thompson et al (1994), Nucleic Acids Res. 22(22):4673-80) or any other suitable program which is suitable to generate sequence alignments. Accordingly, a bacterial lipocalin mutein of any of SEQ ID NOs 1-4 can serve as "subject sequence", while the amino acid sequence of a bacterial lipocalin different from Blc as described herein serves as "query sequence".

Given the above, a skilled artisan is thus readily in a position to determine which amino acid position mutated in Blc as described herein corresponds to an amino acid of a bacterial lipocalin scaffold other than Blc. Specifically, a skilled artisan can align the amino acid sequence of a mutein as described herein, in particular a Blc mutein of the invention with the amino acid sequence of a different bacterial lipocalin to determine which amino acid(s) of said mutein correspond(s) to the respective amino acid(s) of the amino acid sequence of said different lipocalin.

When used herein "a bacterial lipocalin other than Blc" or "a bacterial lipocalin different from Blc" in which one or more amino acid replacements, in particular at one or more position in one, two, three or all four loops, can be made in accordance with the teaching of the present invention encompasses any other bacterial lipocalin known in the art or which can be identified by using Blc as reference sequence, for example, in a BLAST search or using a nucleic acid molecule encoding Blc as probe in, for example, a hybridization experiment.

Preferred bacterial lipocalin scaffolds other than Blc in which one or more amino acid replacements, in particular at one or more position in one, two, three or all four loops, can be made in accordance with the teaching of the present invention can, for example, be retrieved from the bacteria shown in the following Table.

A bacterial lipocalin scaffold other than Blc can be retrieved via the accession number from the bacteria listed in the following Table as follows: A TBLASTN search (Altschul et al., cited herein) using the Blc protein sequence is to be performed on both the microbial genome databases and the non-redundant database at the NCBI website (http://www.ncbi.nlm.nih.gov). The genome sequence 500 bp upstream and downstream of each hit should be retrieved. The six resulting translations are evaluated to identify both the full-length lipocalin sequence and the presence of the 16s ribosomal RNA binding site.

| Bacterial species | Accession Number |
| --- | --- |
| Agrobacterium tumefaciens | NC_003063 |
| Caulobacter crescentus | NC_002696 |
| Mesorhizobium loti | NC_002678 |
| Rhodobacter sphaeroides | AAAE01000158 |
| Rhodospirillum rubrum | AAAG0200000 |
| Silicibacter | NZ_AAFG01000010 |
| Acidovorax (partial) | AB044565 |
| Bordetella | NC_002927 |
| Bordetella parapertussis | NC_002928 |
| Burkholderia cepacia | AAEH01000003 |
| Burkholderia fungorum | NZ_AAAJ03000001 |
| Chromobacterium violaceum | NC_005085 |
| Dechloromonas aromatica | AADF01000001 |
| Methylobacillus flagellatus | AADX01000001 |
| Ralstonia eutropha | AADY01000001 |
| Rubrivivax gelatinosus | AAEM01000005 |
| Thiobacillus denitrificans | AAFH01000001 |
| Citrobacter braakii (partial) | AF492447 |
| Citrobacter freundii | U21727 |
| Citrobacter murliniae | AJ607409 |
| Enterobacter nimipressuralis | AJ487975 |
| Enwinia carotovora | BX950851 |
| Escherichia coli | P39281 |
| Francisella tularensis | AY774926 |
| Idiomarina loihiensis | NC_006512 |
| Klebsiella oxytoca | Y17716 |
| Pseudomonas | AABQ0700000 |
| Pseudomonas | AAAT0300000 |
| Pseudomonas putida | NC_002947 |
| Pseudomonas syingae | AABP02000002 |
| Salmonella typhi | NC_006511 |
| Salmonella typhimurium | AE008903 |
| Shewanella oneidensis | AE015615 |
| Shigella flexneri | NC_004741 |
| Vibrio cholerae | NC_002506 |
| Rubrivivax gelatinosus | AAEM0100000 |
| Thiobacillus denitrificans | AAFH01000001 |
| Acinetobacter | CR543861 |
| Azotobacter vinelandii | NZ_AAAU02000004 |
| Citrobacter braakii (partial) | AF492447 |
| Citrobacter freundii | U21727 |
| Citrobacter murliniae | AJ607409 |
| Enterobacter | AJ487975 |
| Erwinia carotovora | BX950851 |
| Escherichia coli | P39281 |
| Francisella tularensis | AY774926 |
| Idiomarina loihiensis | NC_006512 |
| Klebsiella oxytoca | Y17716 |
| Pseudomonas aeruginosa | AABQ07000004 |

-continued

| Bacterial species | Accession Number |
| --- | --- |
| Pseudomonas fluorescens | AAAT03000001 |
| Pseudomonas putida | NC_002947 |
| Acinetobacter | CR543861 |
| Azotobacter vinelandii | NZ_AAAU02000004 |
| Vibrio parahaemolyticus | NC_004605 |
| Vibrio vulnificus | NC_004460 |
| Xanthomonas axonopodis (1) | NC_003919 |
| Xanthomonas campestris (1) | NC_003902 |
| Bdellovibrio | NC_005363 |
| Desulfotalea psychrophila | NC_006138 |
| Geobacter sulfurreducens | NC_002939 |
| Campylobacter jejuni | AL139078 |
| Campylobacter lari | NZ_AAFK01000002 |
| Chlorobium lepidum | NC_002932 |
| Bacteroides fragilis | NC_006347 |
| Bacteroides | NC_004663 |
| Cytophaga hutchinsonii | AABD03000002 |
| Parachlamydia | NC_005861 |
| Gloeobacter violaceus | NC_005125 |
| Corynebacterium efficiens | NC_004369 |
| Corynebacterium glutamicum | NC_003450 |
| Nocardia farcinica | NC_006361 |
| Bacillus subtilis | P54945 |

The present invention also relates to a nucleic acid coding for the one or more mutein (s) of the bacterial lipocalin protein, which nucleic acid results from mutagenesis. Preferably, said nucleic acid is operably fused at the 3'end a gene coding for the coat protein pIII of a filamentous bacteriophage of the M13-family or coding for a fragment of this coat protein, in order to select at least one mutein for the binding of the given target.

in another aspect, the present invention relates a bacterial lipocalin mutein as described herein which is conjugated to a label selected the group consisting of an organic molecule, an enzyme label, radioactive label, fluorescent label, chromogenic label, luminescent label, a hapten, digoxigenin, biotin, metal complexes, metals, and colloidal gold.

In yet another aspect, the present invention relates to a fusion protein comprising a bacetrial lipocalin mutein or the present invention, wherein an enzyme, a protein or a protein domain, a peptide, a signal sequence and/or an affinity tag is operably fused to the amino terminus or the carboxy terminus of said bacterial lipocalin mutein Also, the present invention relates to a nucleic acid molecule encoding said fusion protein.

Moreover, the present invention relates to a pharmaceutical composition comprising a bacterial lipocalin mutein as described herein or a fusion protein as described herein and a pharmaceutically acceptable carrier or excipient Furthermore, the present invention relates to a method for producing a bacterial lipocalin mutein or a fusion protein thereof, wherein the mutein or the fusion protein thereof is produced starting from the nucleic acid encoding the mutein by means of genetic engineering methods in a bacterial or eukaryotic host organism and is isolated from this host organism or its culture.

Finally, the present invention contemplates a use of a mutein of bacterial lipocalin or a fusion protein thereof for the detection of a given target, comprising the steps of contacting the mutein with a sample suspected of containing the given target under suitable conditions, thereby allowing formation of a complex between the mutein and the given target, and determining the complexed mutein by a suitable signal. The given target may be a protein or protein domain, a peptide, a nucleic acid molecule, an organic molecule or a metal complex and the detection is preferably carried out for validation of the protein as pharmacological drug target.

All references cited herein are hereby incorporated in their entirety.

The present invention is further illustrated by, though in no way limited to, the following examples.

EXAMPLES

Example 1

Recombinant Expression and X-Ray Structure Determination of Blc

Blc was secreted as a soluble protein into the periplasm of *E. coli* after its original type II signal peptide had been exchanged by the type I signal peptide of OmpA (Ghrayeb et al., 1984), which has proven useful for recombinant protein export. In addition, the Cys residue at position 1 of the mature polypeptide, which otherwise carries the lipid anchor of the natural lipoprotein, was replaced by Ala and the unpaired internal thiol residue Cys 113 was substituted by Ser. Purification from the bacterial periplasmic extract was achieved via streptavidin affinity chromatography employing the Strep-tag II (Schmidt & Skerra, 2007), which had been appended to the C-terminus. Blc was finally obtained as a homogeneous protein by preparative gel filtration.

During this purification step we noted that our recombinant Blc elutes as a fully monomeric protein. This was confirmed by analytical size exclusion chromatography (SEC; data not shown), revealing an apparent size of 13.0 kDa, which was even smaller than the calculated mass of 19.1 kDa for the mature protein and clearly indicating the absence of a dimer. Consequently, its oligomerization behaviour was further investigated by means of analytical ultracentrifugation (AUC), resulting in a monomeric molecular mass of 18.7±0.4 kDa. This demonstrated that our recombinant Blc forms a stable monomer in solution, at least up to a concentration of about 40 µM.

Crystallization of Blc was achieved at pH 7.5 with PEG 10000 as precipitant. The obtained crystals belonged to the space group $I4_122$ containing one molecule per asymmetric unit. These crystals showed a lattice packing different from the previously described crystals of Blc-X in space group $P2_12_12_1$ with two molecules in the asymmetric unit. Interpretable main chain electron density for Blc was observed for 149 of 168 residues present in the construct. Missing residues comprised the N-terminal amino acids 1 to 8 and the C-terminal amino acids 158 to 168, i.e. the entire Strep-tag The overall structure of the recombinant Blc analyzed here was very similar to the one of Blc-X (PDB entries 1QWD and 2ACO), revealing the typical lipocalin fold characterized by a β-barrel with eight anti-parallel strands (designated A-H) and a C-terminal α-helix (FIG. 1). In contrast, however, our structure clearly lacked the first two artificial β-stands (designated -1 and 1, respectively) outside the β-barrel that were previously described for Blc-X. This Blc variant, Blc-X, carried 18 additional residues at the N-terminus (thereof 9 visible in the crystallographic model; PDB entry 2ACO) as well as 4 amino acid replacements at the beginning of the mature sequence, both originating from the attB1 Gateway® recombination sequence on the expression vector pDest17 (Campanacci et al., 2006). Together with a stretch of the following native sequence, a two-stranded extra antiparallel β-sheet is formed in the crystal structure of Blc-X (FIGS. 1 and 2). The recombinant Blc prepared in the present study, however, lacked this extra peptide segment and had an almost native N-terminus, except for the missing lipid anchor at Cys 1 (data not shown).

Superposition of Blc with the two non-symmetrical monomers A and B of the Blc-X crystal structure (PDB entry 2ACO) resulted in an r.m.s.d. (over 149 Cα positions) of 0.68 Å and 0.89 Å, respectively, while mutual superposition of the latter two monomers yielded an r.m.s.d. of 1.07 Å. Beside the artificial N-terminus in Blc-X, the largest conformational differences were observed in the E/F-loop, which was well ordered in our structure. This loop, which connects strands E and F of the β-barrel at its open end, adopted a distinct conformation in each of the three X-ray structures, apparently influenced by the differing crystal-packing environment (FIG. 1). Further deviations were observed at the loop regions connecting β-strands A-B and C-D, indicating increased flexibility, which has also been described for other members of this protein family, for example human tear lipocalin (Breustedt et al., 2009). The differing conformations of the A/B- and E/F-loops are critical for ligand binding as their arrangement restricts the accessibility of the deep ligand pocket. Only in monomer B of the Blc-X crystal structure the A/B- and E/F-loops adopt a conformation that allows ligand binding. In our Blc structure and in monomer A of the Blc-X structure, the cavity is mostly shielded by the three Phe residues 35, 90, and 91.

Example 2

Reassessment of the Proposed Dimerization Mechanism for Blc

Previous studies of Blc-X indicated a dimeric state both in the crystal lattice as well as in solution, suggesting formation of an asymmetric functional homodimer with different affinities of its two subunits for lipid ligands (Campanacci et al., 2004; Campanacci et al., 2006). In contrast, we observed Blc as a monomeric protein not only in the new crystal form, but also in solution. To thoroughly compare the previously published Blc-X dimer interface with similar crystal packing contacts in our Blc structure, we performed molecular surface and interaction analyses using PISA (Krissinel & Henrick, 2007).

The dimer interface of Blc-X (PDB entry 2ACO) is formed by 19 and 22 residues for molecules A and B, respectively, involving the N-terminal extra peptide segment together with the ET loop and leading to 709 Å$^2$ and 792 Å$^2$ buried surface area (BSA). These numbers are smaller than the ones of 786 Å$^2$ and 825 Å$^2$ reported before (Campanacci et al., 2006), which may be attributed to different, in part undisclosed, algorithms used. However, an even larger discrepancy was observed for the total solvent accessible surface area (ASA) of the two Blc-X monomers. Using PISA, we calculated a total ASA of 8635 and 8784 Å$^2$, for molecules A and B, respectively, compared with the published number of 7800 Å$^2$ per monomer (Campanacci et al., 2006). Similar larger values were obtained with the programs DSSP (Kabsch & Sander, 1983) and ArealMol (CCP4, 1994).

Based on our calculations, on average 8.6% of the total ASA of Blc-X becomes buried at the interface of the two monomers A and B. In contrast, in the new $I4_122$ crystals Blc forms its tightest contact with a symmetry-related monomer in a neighbouring unit via a different surface region, around the N-terminus of strand A and the preceding loop that crosses the bottom of the β-barrel (not shown). This contact is accompanied by a significantly smaller BSA of 569 Å$^2$, which corresponds to merely 7.0% of the total ASA (8077 Å$^2$).

A striking feature of the previously described Blc-X dimer interface is the two-stranded antiparallel β-sheet that originates from the artificial 22 N-terminal residues. This small extra β-sheet itself neither interacted with the second monomer nor was involved in interactions with symmetry-related neighbours.

However, the hairpin loop that connects the two β-strands seemed to be important for dimer formation of Blc-X (FIG. 2): the loop of molecule B intimately interacted with molecule A, while the same loop of molecule A did not participate in an equivalent interaction, in line with the asymmetry of the dimer noted before (Campanacci et al., 2006). When all the artificially introduced N-terminal residues of molecule B were omitted from the surface analysis, the BSA became significantly reduced to 608 and 686 Å$^2$ for molecules A and B, respectively, that is 7.0% and 8.0% of the total ASA. These smaller values would hardly be significant for a true oligomeric state (Miller et al., 1987). Moreover, the latter numbers were in a similar range as another crystal contact in the P2$_1$2$_1$2$_1$ space group with BSAs of 618 Å$^2$ and 606 Å$^2$ for molecules A and B, respectively, corresponding to 7.2% and 7.0% of ASA.

Taken together, two structural features became evident for Blc-X: (i) its N-terminal extension gives rise to the additional β-sheet, which conformationally fixes the loop in between, and (ii) substitution of the first four residues Cys-Ser-Ser-Pro of wild-type Blc by Lys-Ala-Gly-Ser within this loop leads to a unique intermolecular interaction (FIG. 2) which possibly also stabilizes Blc-X dimer formation in solution. In contrast, the C-terminal Strep-tag II, employed for affinity purification of Blc in our study, is far away from the N-terminus (at least 35 Å distance) and structurally disordered, thus clearly lacking defined interactions with neighbouring molecules in the I4$_1$22 crystal lattice.

The dimer interface of Blc-X was further dominated by the interaction between the E/F-loops of monomers A and B, which contributed 375 and 422 Å$^2$ BSA, respectively, corresponding to ca. 53% of the total contact region including the N-terminal hairpin loop. Due to the asymmetry of the dimer the E/F loop adopted a distinct conformation in each monomer (FIG. 1). Analysis of the alternative crystal packing of Blc in the space group I4$_1$22 revealed that a comparable but distinct contact occurred there with a symmetry mate, related via a crystallographic two-fold axis (data not shown). This crystal contact showed a total BSA of 480 Å$^2$ and was again dominated by the E/F-loop (residues 88-96), with a local BSA of 336 Å$^2$ on each molecule corresponding to 70% of the total BSA in this region. Notably, in the new Blc structure the E/F-loop showed a conformation different from both Blc-X monomers (FIG. 1), suggesting structural flexibility. Therefore, dimerization via the E/F-loop should be entropically disfavoured in solution. The fact that a crystal contact involving the E/F-loop was observed in both crystal structures may be solely attributed to its largely hydrophobic nature.

Example 3

Comparison of Blc to ApoD

Mammalian apolipoprotein D (ApoD) is the closest eukaryotic homologue of Blc and also anchored in a lipid micelle, albeit via a different mechanism (Eichinger et al., 2007).

Structural comparison between Blc and ApoD resulted in 139 matching Cα-positions out of 149 resolved residues in the Blc structure, with an overall r.m.s.d. of 1.37 Å (data not shown). Differences between the two lipocalin structures were mainly observed in the strand connecting loop regions at the open end of the β-barrel. The loops A/B and, in particular, G/H showed the largest deviations. Loop G/H formed an extended hairpin structure in ApoD resulting in a wider pocket, ideally shaped for accommodation of a steroid ligand. On the other hand, the A/B loop, which has a one-residue insertion in Blc compared to ApoD, partially shielded the ligand pocket in the bacterial counterpart. Beside variations in pocket size and accessibility, there were differences in surface hydrophobicity. While ApoD showed distinct hydrophobic patches, which were likely involved in high density lipoprotein (HDL) micelle association (Eichinger et al., 2007), hydrophobic surface areas of Blc were mainly confined to the interior of its cavity. This is in agreement with Blc's presumed function to bind fatty acid-like ligands (Campanacci et al., 2006) whereas membrane association by its N-terminal lipid anchor.

Example 4

Blc Vector Construction

The coding sequence for Blc was amplified from genomic DNA of *E. coli* K12 strain TG1/F$^-$ (Kim et al., 2009) via PCR according to a published procedure (Skerra, 1992) by using phosphorothioate primers 5'-CCG CCA GTT CTC CTA CGC CGC CG-3' (also introducing the Cys1 to Ala mutation) (SEQ ID NO. 5) and 5'-GCT ACC AGG CTG CTG TAC CC-3' (SEQ ID NO. 6) The unique amplification product was purified by agarose gel electrophoresis, phosphorylated with T4 polynucleotide kinase (New England Biolabs, Beverly, Mass.), and ligated with the expression vector pASK75-strepII (Skerra, 1994; Schmidt & Skerra, 2007), which had been cut with StuI and Eco47III and dephosphorylated using shrimp alkaline phosphatase (USB, Cleveland, Ohio). After transformation of *E. coli* XL1-Blue (Bullock et al., 1987) the resulting plasmid, designated pBlc1, was isolated and its composition was confirmed by restriction digest as well as double-stranded dideoxy-sequencing (ABI PRISM 310 Genetic Analyzer; Applied Biosystems, Foster City, Calif.). On pBlc1, the recombinant protein was encoded in fusion with the amino-terminal type I signal peptide of OmpA and the C-terminal Strep-tag II of nine residues (Breustedt et al., 2006; Schmidt & Skerra, 2007). The codon for the unpaired internal thiol residue Cys113 (numbering according to the mature full length protein; Swiss-Prot entry P0A901) was subsequently replaced by a Ser codon via site-directed mutagenesis (Geisselsoder et al., 1987) with the oligodeoxynucleotide 5'-GGT CCG GCC CGC TAA CCA GCG CAT G-3' (SEQ ID NO. 7), finally yielding pBlc2, which was used for recombinant protein production throughout this study.

Example 5

Blc Protein Production and Purification

Recombinant Blc was produced in the *E. coli* K-12 strain JM83 (Yanisch-Perron et al., 1985) harbouring pBlc2 by secretion as a soluble protein into the bacterial periplasm. Shake flask cultures were grown in 21 LB medium supplemented with 100 mg/l ampicillin at 22° C. Gene expression was induced at a cell density of $OD_{550}$=0.5 by adding 0.2 mg/l anhydrotetracycline (Skerra, 1994). After further shaking for 3 h the cells were harvested by centrifugation, resuspended in 500 mM sucrose, 1 mM EDTA, 100 mM Tris-HCl pH 8.0, and kept on ice for 30 min. The resulting spheroplasts were sedimented by centrifugation and the supernatant containing the recombinant protein was recovered. The protein extract was dialyzed against 150 mM NaCl, 1 mM EDTA, 100 mM Tris-HCl pH 8.0 and applied to a Strep-Tactin affinity column (Schmidt & Skerra, 2007) using the same buffer. The recombinant Blc was competitively eluted by application of 2.5 mM D-desthiobiotin in the chromatography buffer. Elution fractions were concentrated, applied to a preparative Superdex 75 gel filtration column (GE Healthcare, Uppsala, Sweden) using 150 mM NaCl, 1 mM EDTA, 100 mM Tris-HCl pH 8.0 as running buffer, and eluted in a homogeneous peak. The yield was ca. 1.5 mg of purified protein per 1 l *E. coli* culture.

Example 6

Blc Biochemical Characterization

Analytical size exclusion chromatography (SEC) was carried out on a Tricorn S75 column (Superdex 75 10/300 GL, bed volume $V_t$=24 ml; GE Healthcare) at a flow rate of 0.5 ml/min using ÄKTA Purifier instrumentation (GE Healthcare) with PBS (4 mM $KH_2PO_4$, 16 mM $Na_2HPO_4$, 115 mM NaCl) as running buffer. Bovine serum albumin (66 kDa, $V_r$=9.861 ml), carbonic anhydrase (29 kDa, $V_r$=12.35 ml), myoglobin (17.05 kDa, $V_r$=13.244 ml), cytochrome C (12.4 kDa, $V_r$=14.11 ml), and aprotinin (6.5 kDa, $V_r$=16.35 ml) were used as protein size standards for calibration of the column while the void volume was determined with blue dextran ($V_0$=8.08 ml).

Sedimentation equilibrium experiments were performed using an XL-I analytical ultracentrifuge and a Ti-60 rotor equipped with a UV/Vis as well as interference detector (Beckman, Fullerton, Calif.). An 0.8 mg/ml solution of the purified recombinant Blc in 150 mM NaCl, 1 mM EDTA, 100 M Tris/HCl pH 8.0 was applied to six-sector 12 mm path length cells. The samples were centrifuged at 25000 rpm for 72 h at 4° C., until equilibrium was reached, whereby the protein gradient was measured by UV absorption at 280 nm. Data analysis was carried out with Kaleidagraph software (Synergy Software, Reading, Pa.) as previously described (Zander et al., 2007; Stromer et al., 2004) using a value of 0.73 ml/g for the specific volume of the protein.

Example 7

Blc Crystallization and Structure Determination

Blc crystals were grown in hanging drops using the vapour diffusion technique. Drops mixed from 1 μl protein solution (10 mg/ml, dialyzed against 10 mM Tris-HCl pH 8.0) and 1 μl reservoir solution were equilibrated against 0.5 ml reservoir solution on siliconized glass cover slips. After about two months at 20° C., two crystals were obtained in the presence of 20% (w/v) PEG 10000, 100 mM HEPES-NaOH pH 7.5. Blc crystals were harvested using Nylon loops (Hampton Research, Laguna Niguel, Calif.), cryoprotected with Paratone N (Hampton Research)—thereby removing excess mother liquor—and frozen in a 100 K nitrogen stream (Oxford Cryosystems, Oxford, UK).

A native data set was collected on a mar345 imaging plate detector (MarResearch, Hamburg, Germany) using monochromatic Cu-$K_\alpha$ radiation from a RU-300 rotating anode generator (Rigaku, Tokyo, Japan) equipped with Confocal Max-Flux Optics (Osmic, Troy, Mich.). Diffraction data were processed with the XDS Package (Kabsch, 1993). The Blc crystals belonged to the space group $I4_22$ with unit cell parameters a=b=88.94 Å, and c=78.35 Å, containing one protein molecule per asymmetric unit (Table 1). The X-ray structure was solved by molecular replacement as implemented in PHASER (Storoni et al., 2004) using the coordinates of a published Blc structure (PDB code 1QWD) after deleting the N-terminal residues −17 to 4 as well as loop residues 33 to 38 and 60 to 69 at the open end of the β-barrel. Model building was performed with Coot (Emsley & Cowtan, 2004), followed by restrained and TLS refinement using REFMAC5.5 (Murshudov et al., 1997; Winn et al., 2001). Total B values were calculated with TLSANL (Howlin et al., 1993). Finally, the structure was validated with Coot and MolProbity (Davis et al., 2007).

Graphics were prepared with PyMOL (DeLano, 2002) while secondary structure elements were assigned with DSSP (Kabsch & Sander, 1983). Superposition of structures was performed with SUPERPOSE (Krissinel & Henrick, 2004) and interfaces were analyzed with PISA (Krissinel & Henrick, 2007). The coordinates and structure factors for the refined Blc structure have been deposited at the RCSB Protein Data Bank (PDB accession code 3MBT).

REFERENCES

Beste et al, (1999). Small antibody-like proteins with prescribed ligand specificities derived from the lipocalin fold. Proc. Natl. Acad. Sci. USA 96, 1898-1903.

Bishop, R. E., Penfold, S. S., Frost, L. S Holtje, J. V. & Weiner, J. H. (1995). J Biol Chem 270, 23097-23103.

Bishop, R. E. (2000). Biochim Biophys Acta 1482, 73-83.

Breustedt, D. A., Schönfeld, D. L. & Skerra, A. (2006). Biochim Biophys Acta 1764, 161-173.

Breustedt, D. A., Chatwell, L. & Skerra, A. (2009). Acta Crystallogr D Biol Crystallogr 65, 1118-1125.

Bullock, W. O., Fernandez, J. M. & Short, J. M. (1987). Biotechniques 5, 376-379.

Campanacci, V., Nurizzo, D., Spinelli, S., Valencia, C., Tegoni, M. & Cambillau, C. (2004). FEBS Lett 562, 183-188.

Campanacci, V., Bishop, R. E., Blangy, S., Tegoni, M. & Cambillau, C. (2006). FEBS Lett 580, 4877-4883.

CCP4 (1994). Acta Crystallogr Sect D Biological Crystallography 50, 760-763.

Davis, I. W., Leaver-Fay, A., Chen, V. B., Block, J. N., Kapral, G. J., Wang, X., Murray, L. W., Arendall, W. B., 3rd, Snoeyink, J. Richardson, J. S. & Richardson, D. C. (2007). Nucleic Acids Res 35, W375-383.

DeLano, W. L. (2002). DeLano Scientific.

Eichinger, A., Nasreen, A., Kim, H. J. & Skerra, A. (2007). J Biol Chem 282, 31068-31075.

Emsley, P. & Cowtan, K. (2004). Acta Crystallogr D Biol Crystallogr 60, 2126-2132.

Flower, D. R. (1996). Biochem J 318, 1-14.

Flower, D. R., North, A. C. & Sansom, C. E. (2000). Biochim Biophys Acta 1482, 9-24.
Geisselsoder, J., Witney, F. & Yuckenberg, P. (1987). Biotechniques 5, 786-790.
Ghrayeb, J., Kimura, H., Takahara, M., Hsiung, H., Masui, Y. & Inouye, M. (1984). EMBO J 3, 2437-2442.
Groat, R. G., Schultz, J. E., Zychlinsky, E., Bockman, A. & Matin, A. (1986). J Bacteriol 168, 486-491
Howlin, B., Butler, S. A., Moss, D. S., Harris, G. W. & Driessen, H. P. C. (1993). J Appl Crystallogr 26, 622-624.
Huijbregts, R. P., de Kroon, A. I. & de Kruijff, B. (2000). Biochim Biophys Acta 1469, 43-61.
Kabsch, W. & Sander, C. (1983). Biopolymers 22, 2577-2637.
Kabsch, W. (1993). J Appl Crystallogr 26, 795-800.
Kim, H. J., Eichinger, A. & Skerra, A. (2009). J Am Chem Soc 131, 3565-3576.
Krissinel, E. & Henrick, K. (2004). Acta Crystallogr D Biol Crystallogr 60, 2256-2268.
Krissinel, E. & Henrick, K. (2007). J Mol Biol 372, 774-797.
Miller, S., Lesk, A. M., Janin, J. & Chothia, C. (1987). Nature 328, 834-836.
Murshudov, G. N., Vagin, A. A. & Dodson, E. J. (1997). Acta Crystallogr D Biol Crystallogr 53, 240-255.
Schmidt, T. G. & Skerra, A. (2007). Nat Protoc 2, 1528-1535.
Schönfeld, D., Matschinerm, G., Chatwell, L., Trenthmann, S., Gille, H., Hülsmeyer, M., Brown, N., Kaye, P. M., Schlenhuber, S., Hohlbaum, A. M. & Skerra, A., (2009). PNAS 106 (20), 8198-8203.
Skerra, A. (1992). Nucleic Acids Res 20, 3551-3554.
Skerra, A. (1994). Gene 151, 131-135.
Skerra, A. (2000). Biochim Biophys Acta 1482, 337-350.
Storoni, L. C., McCoy, A. J. & Read, R. J. (2004). Acta Crystallogr D Biol Crystallogr 60, 432-438.
Stromer, T., Fischer, E., Richter, K., Haslbeck, M. & Buchner, J. (2004). J Biol Chem 279, 11222-11228.
Tao, P., Wang, R. X. & Lai, L. H. (1999). J Mol Model 5, 189-195
Tokuda, H. & Matsuyama, S. (2004). Biochim Biophys Acta 1693, 5-13.
Winn, M. D., Isupov, M. N. & Murshudov, G. N. (2001). Acta Crystallogr D Biol Crystallogr 57, 122-133.
Yanisch-Perron, C., Vieira, J. & Messing, J. (1985). Gene 33, 103-119.
Zander, H., Hettich, E., Greiff, K., Chatwell, L. & Skerra, A. (2007). FEBS J 274, 2603-2613.

TABLE 1

Data collection and refinement statistics for Blc.

| Data collection | |
| --- | --- |
| Space group | $I4_122$ |
| Unit cell parameters [Å] | a = b = 88.94, c = 78.35 |
| Wavelength [Å] | 1.5418 |
| Resolution [Å] | 30-2.6 (2.7-2.6)$^a$ |
| Completeness [%] | 98.7 (99.8) |
| Unique reflections | 5024 (531) |
| Multiplicity | 6.1 (6.2) |
| Mean I/σ(I) | 34.7 (9.4) |
| $R_{meas}$ [%]$^b$ | 4.5 (20.1) |
| Wilson B-factor [Å$^2$] | 36.4 |
| Refinement | |
| Resolution [Å] | 18.70-2.60 (2.67-2.60)$^a$ |
| Reflections (working) | 4787 (343) |
| Reflections (test) | 236 (16) |
| $R_{cryst}$ [%]$^c$ | 22.2 (30.6) |
| $R_{free}$ [%]$^d$ | 27.6 (46.0) |
| Number of protein atoms/water molecules | 1209/18 |
| B-values of protein atoms/water mols [Å$^2$] | 36.0/11.7 |
| Ramachandran plot: favoured/outliers [%] | 93.2/0.0 |
| Rmsd bonds [Å]/angles [°] | 0.009/1.227 |

$^a$Values in parentheses represent the highest resolution shell.

$^b$
$$R_{meas} = \frac{\sum_{hkl} \sqrt{\frac{n}{n-1} \sum_{j=1}^{n} |I_{hkl,j} - \langle I_{hkl} \rangle|}}{\sum_{hkl} \sum_{j} I_{hkl,j}}$$

$^c$
$$R_{cryst} = \frac{\sum_{hkl} |F_{hkl}^{obs} - F_{hkl}^{calc}|}{\sum_{hkl} F_{hkl}^{obs}}$$

$^d R_{free}$ is calculated as for $R_{cryst}$, but with 5% of the reflections excluded from the refinement

What is claimed is:

1. A composition comprising a plurality of monomeric bacterial lipocalin (Blc) muteins, wherein said Blc muteins differ from each other in at least one amino acid at a position within at least one loop region of a Blc polypeptide, wherein the four loop region of said Blc polypeptide are at amino acid positions corresponding to positions 27-43, 58-73, 88-96, and 113-121 of the mature Blc polypeptide set forth in SEQ ID NO: 4, wherein said plurality of Blc muteins comprise at least 50 different polypeptide molecules, and wherein said Blc muteins are within at least 75% sequence identity with SEQ ID NO: 4.

2. The composition according to claim 1, wherein said Blc muteins differ from each other in at least one amino acid at a position within at least two loop regions of said Blc polypeptide.

3. A method of isolating a polypeptide of interest, comprising the steps of (i) allowing the composition of claim 1 to be in contact with a target of interest, wherein said polypeptide of interest is comprised within said composition and specifically binds to the target; and (ii) isolating the polypeptide or a polypeptide-target complex resulting from said specific binding.

* * * * *